United States Patent
Sakasegawa et al.

(10) Patent No.: US 7,335,734 B2
(45) Date of Patent: Feb. 26, 2008

(54) PROTEIN POLYMER HAVING UNFOLD ACTIVITY ON HIGHER-ORDER STRUCTURE OF PROTEIN

(75) Inventors: Naomi Sakasegawa, Tokyo (JP); Hiroyuki Sasaki, Kanagawa (JP); Shoichiro Tsukita, Kyoto (JP)

(73) Assignee: Japan Science and Technology Corporation, Saitama (JP)

( * ) Notice: Subject to any disclaimer, the term of this patent is extended or adjusted under 35 U.S.C. 154(b) by 0 days.

(21) Appl. No.: 10/477,118

(22) PCT Filed: May 2, 2002

(86) PCT No.: PCT/JP02/04387

§ 371 (c)(1), (2), (4) Date: Jan. 30, 2004

(87) PCT Pub. No.: WO02/090385

PCT Pub. Date: Nov. 14, 2002

(65) Prior Publication Data

US 2005/0048078 A1     Mar. 3, 2005

(30) Foreign Application Priority Data

May 7, 2001     (JP) .............................. 2001-136610

(51) Int. Cl.
*C07K 1/00*     (2006.01)

(52) U.S. Cl. ..................................................... 530/350
(58) Field of Classification Search ................. 530/350
See application file for complete search history.

(56) References Cited

FOREIGN PATENT DOCUMENTS

WO     96/37621     11/1996
WO     97/15595     5/1997

OTHER PUBLICATIONS

Amberg et al., Submitted (Sep. 1995) to the EMBL/GenBank/DDBJ databases. GeneCore version 5.1.6. ID AIP2 Yeast. AC P46681.*
Pohl T.M., Submitted (Nov. 1995) to the EMBL/GenBank/DDBJ databases. GeneCore version 5.1.6. ID AIP2 Yeast. AC P46681.*
SCORE results, Seq ID No. 1, pp. 1-14.*

* cited by examiner

*Primary Examiner*—Karen Cochrane Carlson
*Assistant Examiner*—Agnes B. Rooke
(74) *Attorney, Agent, or Firm*—Wenderoth, Lind & Ponack, L.L.P.

(57) ABSTRACT

The invention of this application provides a protein polymer of 8 to 15 proteins in association, wherein each protein has the amino acid sequence of SEQ ID NO: 1, and where the protein polymer has an unfold activity on the higher-order structure of a protein and this protein polymer is useful for the development of therapeutic agents of various diseases due to the failure in the formation of the higher-order structure of a protein, and the like.

1 Claim, 6 Drawing Sheets

SEQUENCE LISTING

```
<160> NUMBER OF SEQ ID NOS: 1

<210> SEQ ID NO 1
<211> LENGTH: 530
<212> TYPE: PRT
<213> ORGANISM: Saccharomyces cerevisiae
<300> PUBLICATION INFORMATION:
<308> DATABASE ACCESSION NUMBER: GenBank/Z74226
<309> DATABASE ENTRY DATE: 1997-08-11

<400> SEQUENCE: 1
```

Met Leu Arg Asn Ile Leu Val Arg Ser Thr Gly Ser Asn Phe Lys Phe
 1               5                  10                  15

Ala Gly Arg Tyr Met Lys Ser Ser Ala Leu Leu Gly Tyr Tyr Arg Arg
            20                  25                  30

Val Asn Tyr Tyr Ser Thr Lys Ile Gln Thr Arg Leu Thr Ser Glu Asn
        35                  40                  45

Tyr Pro Asp Val His Arg Asp Pro Arg Phe Lys Lys Leu Thr Ser Asp
    50                  55                  60

Asp Leu Asn Tyr Phe Lys Ser Ile Leu Ser Glu Gln Glu Ile Leu Arg
65                  70                  75                  80

Ala Ser Glu Ser Glu Asp Leu Ser Phe Tyr Asn Glu Asp Trp Met Arg
                85                  90                  95

Lys Tyr Lys Gly Gln Ser Lys Leu Val Leu Arg Pro Lys Ser Val Glu
            100                 105                 110

Lys Val Ser Leu Ile Leu Asn Tyr Cys Asn Asp Glu Lys Ile Ala Val
        115                 120                 125

Val Pro Gln Gly Gly Asn Thr Gly Leu Val Gly Gly Ser Val Pro Ile
    130                 135                 140

Phe Asp Glu Leu Ile Leu Ser Leu Ala Asn Leu Asn Lys Ile Arg Asp
145                 150                 155                 160

Phe Asp Pro Val Ser Gly Ile Leu Lys Cys Asp Ala Gly Val Ile Leu
                165                 170                 175

Glu Asn Ala Asn Asn Tyr Val Met Glu Gln Asn Tyr Met Phe Pro Leu
            180                 185                 190

Asp Leu Gly Ala Lys Gly Ser Cys His Val Gly Val Val Ala Thr
        195                 200                 205

Asn Ala Gly Gly Leu Arg Leu Leu Arg Tyr Gly Ser Leu His Gly Ser
    210                 215                 220

Val Leu Gly Leu Glu Val Val Met Pro Asn Gly Gln Ile Val Asn Ser
225                 230                 235                 240

-continued

```
Met His Ser Met Arg Lys Asp Asn Thr Gly Tyr Asp Leu Lys Gln Leu
            245                 250                 255

Phe Ile Gly Ser Glu Gly Thr Ile Gly Ile Ile Thr Gly Val Ser Ile
            260                 265                 270

Leu Thr Val Pro Lys Pro Lys Ala Phe Asn Val Ser Tyr Leu Ser Val
            275                 280                 285

Glu Ser Phe Glu Asp Val Gln Lys Val Phe Val Arg Ala Arg Gln Glu
            290                 295                 300

Leu Ser Glu Ile Leu Ser Ala Phe Glu Phe Met Asp Ala Lys Ser Gln
305                 310                 315                 320

Val Leu Ala Lys Ser Gln Leu Lys Asp Ala Ala Phe Pro Leu Glu Asp
            325                 330                 335

Glu His Pro Phe Tyr Ile Leu Ile Glu Thr Ser Gly Ser Asn Lys Asp
            340                 345                 350

His Asp Asp Ser Lys Leu Glu Thr Phe Leu Glu Asn Val Met Glu Glu
            355                 360                 365

Gly Ile Val Thr Asp Gly Val Val Ala Gln Asp Glu Thr Glu Leu Gln
            370                 375                 380

Asn Leu Trp Lys Trp Arg Glu Met Ile Pro Glu Ala Ser Gln Ala Asn
385                 390                 395                 400

Gly Gly Val Tyr Lys Tyr Asp Val Ser Leu Pro Leu Lys Asp Leu Tyr
            405                 410                 415

Ser Leu Val Glu Ala Thr Asn Ala Arg Leu Ser Glu Ala Glu Leu Val
            420                 425                 430

Gly Asp Ser Pro Lys Pro Val Val Gly Ala Ile Gly Tyr Gly His Val
            435                 440                 445

Gly Asp Gly Asn Leu His Leu Asn Val Ala Val Arg Glu Tyr Asn Lys
            450                 455                 460

Asn Ile Glu Lys Thr Leu Glu Pro Phe Val Tyr Glu Phe Val Ser Ser
465                 470                 475                 480

Lys His Gly Ser Val Ser Ala Glu His Gly Leu Gly Phe Gln Lys Lys
            485                 490                 495

Asn Tyr Ile Gly Tyr Ser Lys Ser Pro Glu Glu Val Lys Met Met Lys
            500                 505                 510

Asp Leu Lys Val His Tyr Asp Pro Asn Gly Ile Leu Asn Pro Tyr Lys
            515                 520                 525

Tyr Ile
530
```

PROTEIN POLYMER HAVING UNFOLD ACTIVITY ON HIGHER-ORDER STRUCTURE OF PROTEIN

TECHNICAL FIELD

The present invention relates to a protein polymer having an unfold activity for the higher-order structure of a protein which has been intracellularly synthesized (unfold activity), which is useful for the development of therapeutic agents of various diseases due to the failure in the formation of the higher-order structure of a protein (protein aggregation and the like), and the like.

BACKGROUND ART

Amino acids synthesized in biological organisms can function as a protein, only when the polypeptide synthesized from amino acids can form the correct steric structure of the protein. Essentially, the correct formation of the steric structure is consistently, rapidly and efficiently done intracellularly. Cells have a factor promoting the formation of the higher-order structure, which is called the molecular chaperone. Some disadvantage for cells may sometimes occur, such as the insufficiency of molecular chaperone formation or protein denaturation due to the formation of an erroneous sequence. It has been elucidated recently that various diseases emerge because the control system for the higher-order structure of proteins does not work properly.

For example, Alzheimer's disease is a neuropathic disease occurring because the component called amyloid has aggregated together intracellularly. Amyloid generally forms a helix steric structure. In the case of the disease, however, the helix steric structure is transformed into a structure called, cross β structure. Thus, amyloid adheres to each other and accumulates intracellularly, triggering brain nerve damages. Furthermore, neuropathic Huntington's disease occurs, because elongated polyglutamic acid, which are attached to the tail part of the protein, huntintin, due to genetic mutation, is involved in the adhesion of the protein to each other, thereby leading to the failure of cellular functions. Furthermore, it is suggested that the functional impairment of HSP (HSC) as one of molecular chaperones is the pathogenesis of Parkinson's disease, cystic fibrosis, and in some cases of spinocerebellar degeneration.

It has been elucidated that a group of apparently different diseases such as these have the common molecular base, namely the failure in the formation of the higher-order structure of a protein as the underlining pathogenesis. No therapeutic method, which is extremely effective for these diseases, has existed yet. Because any component with an unfolding activity on the higher-order structure of a protein without substrate specificity has not yet been found, protein aggregates, which are the direct cause of such diseases, cannot be targeted and unfolded.

On the other hand, a cell should be so flexible that the structure of protein can be unfolded rapidly during dynamic movements, such as cell migration and cell division. Furthermore, once formed, protein aggregates with an erroneous higher-order structure are quickly unfolded, and transferred to a decomposition system. Although it has been recognized so far that such factor is essential, the factor has not yet been identified, because of the difficulty in the purification thereof.

So as to radically cure various diseases due to the failure in the formation of the higher-order structure of a protein, the aggregation of the diseased protein should essentially be untangled, as described above. It is indispensable therefore that "a factor for unfolding the higher-order structure of a protein" be identified, isolated and purified. Additionally, it is expected that such factor can be used as a very useful material for research in cell biology.

The invention of the application has been achieved in such circumstance. It is an object of the invention to provide a new protein polymer showing a great activity for unfolding the higher-order structure of a protein.

DISCLOSURE OF THE INVENTION

In a first aspect of the invention, the application provides a protein polymer of 8 to 15 proteins in association, each of the proteins having the amino acid sequence of SEQ ID NO: 1, wherein the protein polymer has an unfold activity for the higher-order structure of a protein.

In other words, the protein polymer in the first aspect of the invention (sometimes referred to as YDL178W protein polymer hereinafter) is a protein polymer of 8 to 15, preferably 10 to 12 proteins in association, wherein each protein of the protein polymer has the amino acid sequence of SEQ ID NO: 1 and is transcribed from the open reading frame (ORF) YDL178w (GenBank Accession No. Z74226) of *Saccharomyces cervisiae*.

In a second aspect of the invention, this application provides a protein polymer, wherein each of the proteins of the protein polymer has an amino acid sequence which has been modified from the amino acid sequence of SEQ ID NO: 1 by the deletion of one or more amino acid residues therein or the substitution of one or more amino acid residues therein with other amino acid residues or the addition of one or more amino acid residues thereto. The protein polymer in the second aspect of the invention is a protein polymer having variants of the protein transcribed from *Saccharomyces cerevisiae* ORF YDL178w or a protein transcribed from gene regions with homology to YDL178w in other yeast species or biological species, and has an unfold activity on the intracellular higher-order structure of a protein.

BEST MODE FOR CARRYING OUT THE INVENTION

The protein polymer (YDL178W polymer) in the first aspect of the invention can be obtained by biochemical purification using unfolding activity as the marker of the unfold activity of the subject protein generated by *Saccharomyces cerevisiae*. However, its mass production by genetic engineering technology is preferable.

Specifically, recombination of a yeast expression vector using a DNA fragments encoding *Saccharomyces cerevisiae* ORF YDL178w (GenBank Accession No. Z74226) is done. Then, the recombinant vector is transferred into yeast. From the culture of the transformed yeast, the objective YDL178W polymer is isolated and purified, to thereby recover the objective YDL178W polymer at such an amount that the resulting YDL178W polymer can be used for example for the development of pharmaceutical products.

The recombinant vector can be introduced into yeast by well known methods such as lithium acetate method. So as to recover the objective protein polymer from the transformed yeast, further, a combination of well known processes can be done, including for example treatment with denaturing agents such as urea and surfactants, ultrasonic treatment, enzyme digestion, salting-out and solvent precipitation processes, dialysis, centrifugation, ultra-filtration, gel filtration, SDS-PAGE, isoelectric focusing, ion exchange chromatography, hydrophobic chromatography, affinity chromatography, and reverse phase chromatography. For purification in a simple manner and at high precision, the protein can be expressed while the protein is attached with an oligopeptide tag never influencing the unfold activity, as described below in the following examples.

The protein polymer in the second aspect of the invention can also be recovered by the genetic engineering approach as described above. Specifically, via screening of the genome libraries or cDNA libraries derived from other yeast species or biological species, using the polynucleotide encoding *Saccharomyces cerevisiae* ORF YDL178w or a partial sequence thereof as probe, a gene with homology to *Saccharomyces cerevisiae* ORF YDL178w is identified; then, transferring an expression vector recombined with the gene (polynucleotide) into a host cell, followed by isolation and purification from the culture of the resulting transformed host by know methods, the objective protein polymer can be obtained. Depending on the origin of the polynucleotide to be introduced and the like, a host cell can appropriately be used, including for example *Escherichia coli*, yeast, *Bacillus subtilis*, animal cells and plant cells.

EXAMPLES

The invention of this application is described in more detail and more specifically in the following examples. The following examples never limit the invention.

Example 1

A DNA sequence encoding a polypeptide of 6 histidine molecules was attached as a tag to the terminus of the DNA fragment encoding *Saccharomyces cerevisiae* ORF YDL178w. The resulting DNA fragment was inserted in a yeast expression vector pAUR123 (TaKaRa) to construct a recombinant vector, which was then introduced in yeast. Using the resistance against a drug (Aureobasidin; TaKaRa) as the marker, a transformed yeast strain was selected, which was then cultured in a yeast culture broth (YPD) supplemented with Aureobasidin at a concentration of 0.5 µg/ml. Subsequently, the cultured yeast was recovered, disrupted with glass beads and centrifuged to remove a fraction containing non-disrupted fragments, and was then ultra centrifuged at 100,000×g. The resulting precipitate was purified on a column packed with a resin specifically recognizing the histidine tag (Ni-NTA, Qiagen; or TALON, Clontech; or the like), to obtain the protein molecule generated from the yeast ORF YDL178w.

Example 2

Figure 1:
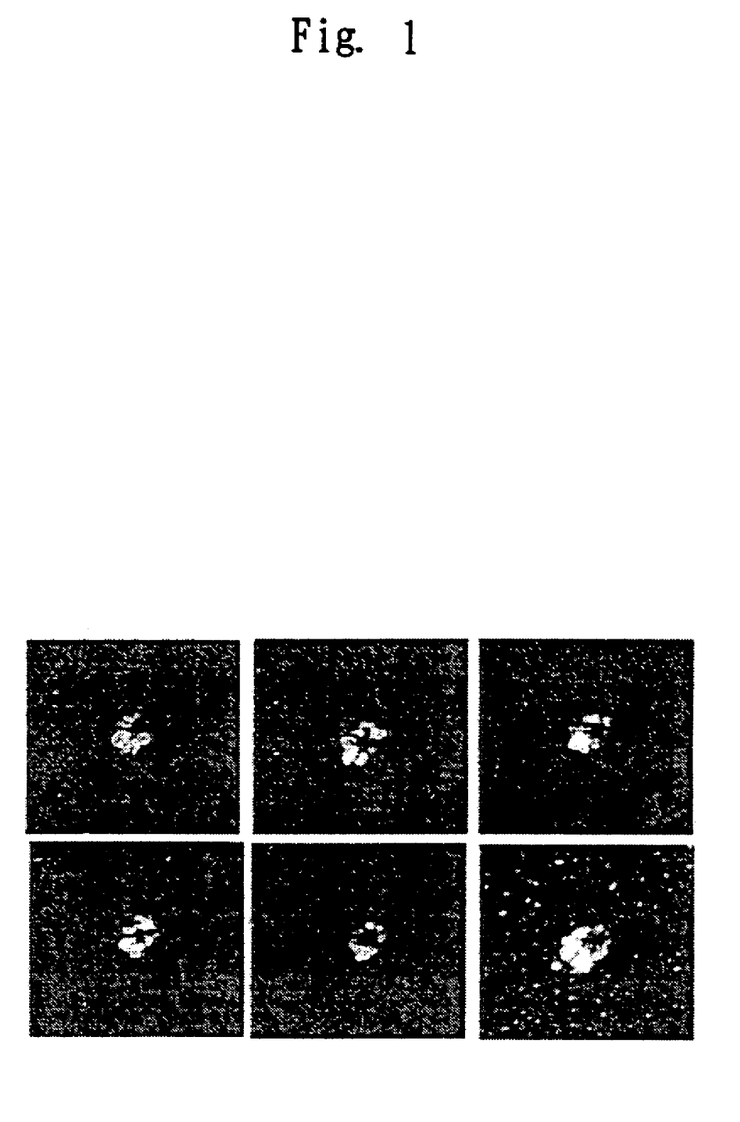
FIG. 1 is an electron microscopic photopicture depicting the structure of the YDL178W polymer of the invention.

The protein molecule derived from the yeast ORF YDL178w as recovered in Example 1 was treated by low angle rotation deposition method, which was then observed with electron microscope. As shown in FIG. 1, consequently, the protein molecule was of a doughnut shape or wrench shape with a hole at the center. It was confirmed that the protein molecule was a polymer of the protein monomers in assembly.

Figure 2:
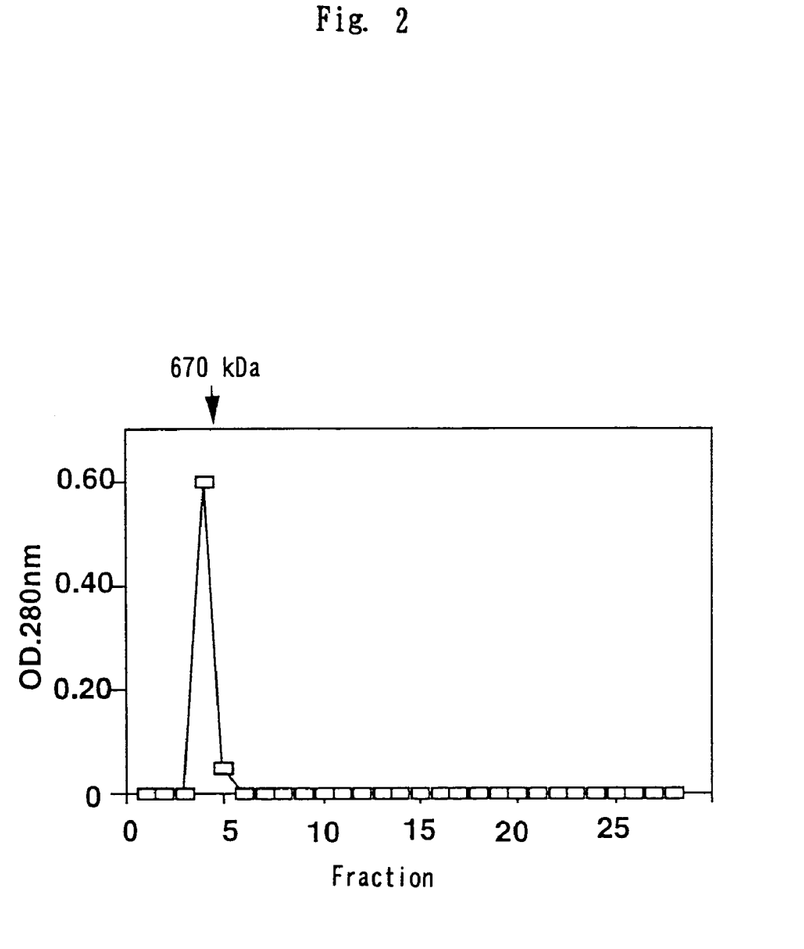
FIG. 2 shows the molecular weight of the YDL178W polymer of the invention as the results of the determination by size exclusion chromatography.

Further confirmation was carried out by size exclusion chromatography. As shown in FIG. 2, consequently, the molecular weight of the protein molecule was about 670 kDa. Because the molecular weight of the protein monomer transcribed from the yeast ORF YDL178w is about 60 kDa, it was confirmed that the protein molecule recovered in Example 1 was a polymer of 10 to 12 monomers in association, each of the monomers being the protein monomer YDL178W.

Example 3

The activity of the YDL178W polymer recovered in Example 1 for unfolding rabbit skeleton muscle-derived myosin was tested.

Figure 3:
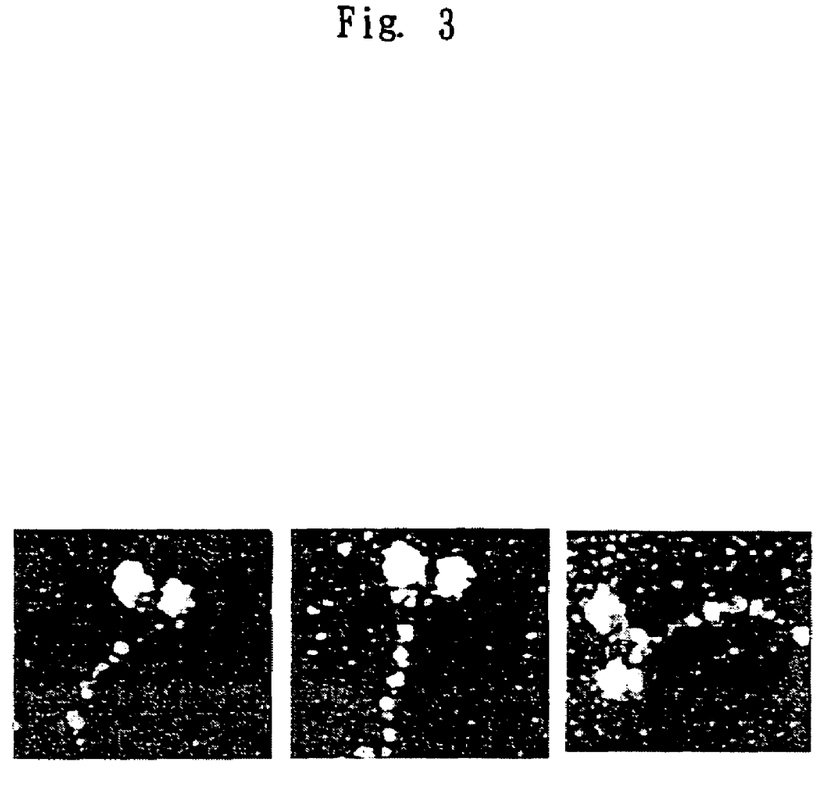
FIG. 3 is an electron microscopic photopicture depicting the structure of rabbit skeletal muscle myosin.

So as to observe one rabbit skeleton-derived myosin molecule with electron microscope, the sample was treated by the low angle rotary shadowing method. As shown in FIG. 3, myosin is of a characteristic higher-order structure with two heads and a tail.

Figure 4:
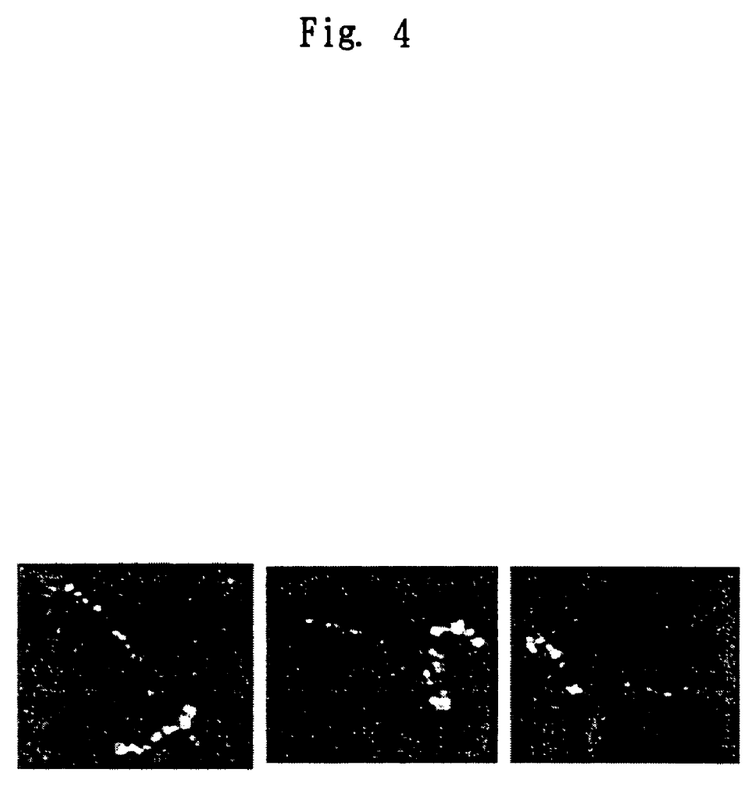
FIG. 4 is an electron microscopic photopicture depicting the structural change of myosin incubated with the YDL178W polymer of the invention.

The YDL178W polymer recovered in Example 1 was incubated with the myosin in the presence of ATP at 30° C. for 15 minutes, and was similarly treated by the low angle rotary shadowing method, for observation with electron microscope. As shown in FIG. 4, consequently, the structure of the myosin molecule was decomposed by the YDL178W polymer at such a state that the head almost completely lost the original shape and the helix structure of the tail was unfolded.

Example 4

It was confirmed via the analysis of the amino acid sequence of SEQ ID NO: 1 of the protein monomer encoded by the yeast ORF YDL178w that the protein contained a sequence for coil formation at the terminus (positions 1293 to 1593 in SEQ ID NO: 1). Because such coil structure is generally used as a tool for self-assembly of a protein, speculatively, the polymer structure of the YDL178W polymer would also be formed with the coil structure.

Figure 5:
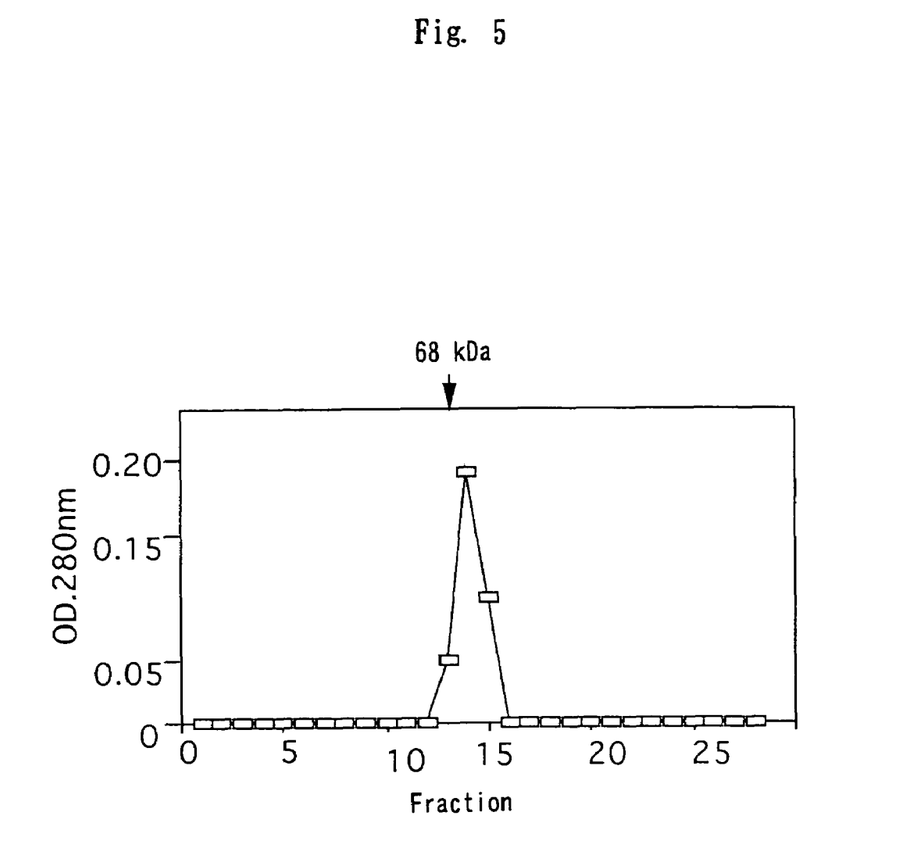
FIG. 5 shows the molecular weight of the protein YDL178-del with deficiency in the coil-forming part as the results of the determination by size exclusion chromatography.

Therefore, the coil-forming sequence was deleted from the DNA sequence of the yeast ORF YDL178w. Then, the resulting deleted DNA fragment was expressed in yeast in a similar manner as in Example 1. The molecular weight of the resulting protein YDL189W-del was determined by size exclusion chromatography. Consequently, as shown in FIG. 5, the molecular weight of the resulting YDL189w-del was about 60 kDa, which is almost similar to the molecular weight of the monomer protein. Thus, it was confirmed that the protein with deficiency in the coil-forming part could not form any polymer.

Figure 6:
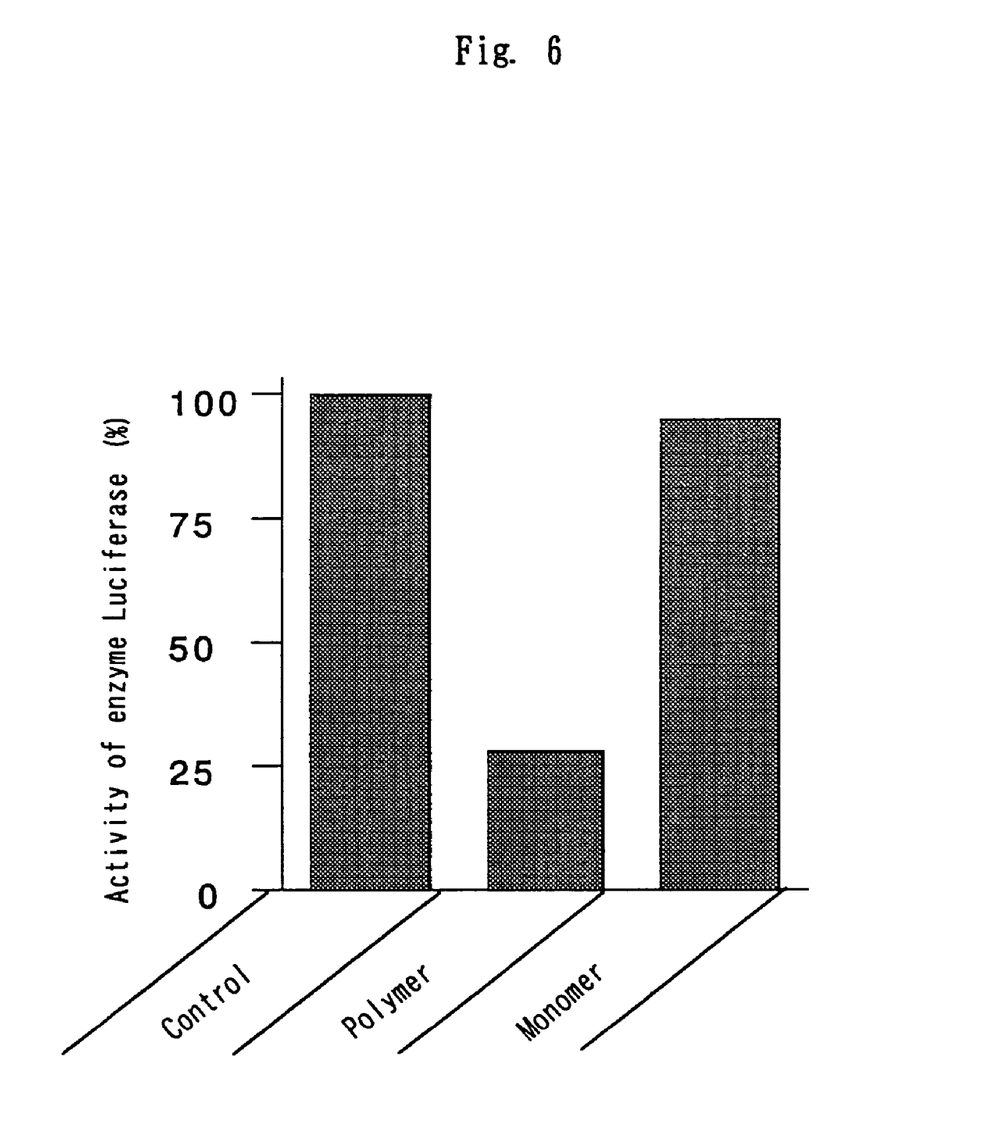
FIG. 6 shows the activity of the enzyme luciferase incubated with the YDL178W polymer of the invention or the protein monomer YDL178W-del.

Subsequently, the unfold activity on the higher-order structure of the protein YDL178w-del was studied. As the substrate, firefly luminescent enzyme luciferase was used, which was incubated in the presence of ATP with YDL178w-del or the YDL178W polymer. Luciferase allows the luminescence of luciferin via the enzyme activity, when the luciferase retains the higher-order structure. The luminescence can be detected with luminometer. As shown in FIG. 6, luciferase incubated with the YDL178W polymer never allowed the luminescence of luciferin. Hence, it was confirmed that the higher-order structure was unfolded with the YDL178W polymer. However, the luciferase incubated with the monomer protein YDL178W-del allowed the detection of the luminescence of luciferin at about the same level as that of control because the higher-order structure was not unfolded.

Based on the above results, it was verified that the formation of the polymer of the protein expressed from the yeast ORF YDL178w was indispensable, for exerting the unfold activity on the higher-order structure of a protein.

INDUSTRIAL APPLICABILITY

As described above in detail, the invention of this application can provide a protein polymer with an unfold activity on the higher-order structure of a protein. The protein polymer is useful for the development of therapeutic agents of various diseases due to the failure in the formation of the higher-order structure of a protein, and the like.

The invention claimed is:

1. A purified protein polymer comprising 8 to 15 proteins in coil formation, wherein each protein has the amino acid sequence of SEQ ID NO: 1, and the protein polymer has an unfold activity for a higher-order structure of a protein.

* * * * *